United States Patent [19]

Wu et al.

[11] 4,096,124

[45] Jun. 20, 1978

[54] ESTERIFICATION PROCESS

[75] Inventors: William C. L. Wu, East Brunswick; Raymond Eichenbaum, Spotswood, both of N.J.

[73] Assignee: Mobil Oil Corporation, New York, N.Y.

[21] Appl. No.: 648,292

[22] Filed: Jan. 12, 1976

Related U.S. Application Data

[63] Continuation of Ser. No. 204,778, Dec. 3, 1971, which is a continuation of Ser. No. 856,898, Sep. 4, 1969, abandoned, which is a continuation of Ser. No. 560,105, Jun. 24, 1966, abandoned, which is a continuation-in-part of Ser. No. 485,561, Sep. 7, 1965, abandoned.

[51] Int. Cl.$^2$ ............................................. C07C 69/82
[52] U.S. Cl. ................................. 260/75 M; 560/94
[58] Field of Search ............. 260/475 P, 75 R, 75 M; 560/94

[56] References Cited

U.S. PATENT DOCUMENTS

| 3,050,533 | 8/1962 | Munro et al. | 260/346.1 |
| 3,060,152 | 10/1962 | Ringwald | 260/75 |
| 3,185,669 | 5/1965 | McKinney | 260/75 |
| 3,185,670 | 5/1965 | McKinney | 260/75 |
| 3,444,140 | 5/1969 | Stewart et al. | 260/75 |

FOREIGN PATENT DOCUMENTS

| 1,297,516 | 5/1962 | France. | |
| 777,628 | 6/1957 | United Kingdom | 260/475 P |

*Primary Examiner*—Jane S. Myers
*Attorney, Agent, or Firm*—Charles A. Huggett

[57] ABSTRACT

Terephthalic acid is esterified with an alkylene glycol by heating in a first stage one mole of the acid with at least about 1.2 moles of the glycol and 0.01 to 1.0% based on the weight of the acid of a volatile organic base at a temperature between 240° and 320° C and at a pressure above the vapor pressure of the glycol at the reaction temperature until about 75–85% of the acid groups initially present in the terephthalic acid have been esterified, and then maintaining the reaction mixtures from the first stage in a second stage at a temperature between 240° to 320° at a pressure less than that of the said first stage until at least about 95% of the acid groups initially present in the terephthalic acid have been esterified.

21 Claims, No Drawings

ESTERIFICATION PROCESS

This application is a continuation of co-pending application Ser. No. 204,778, filed Dec. 3, 1971 which was a continuation of application Ser. No. 856,898, filed Sept. 4, 1969, now abandoned, which was a streamlined continuation of application Ser. No. 560,105, filed June 24, 1966, now abandoned, which, in turn, was a continuation-in-part of application Ser. No. 485,561, filed Sept. 7, 1965, now abandoned.

This invention relates to a process for making intermediate esters of terephthalic acid useful in the production of film- and fiber-forming linear polyesters.

Fiber-forming polyethylene terephthalate, for example, is usually prepared commercially by means of a two-step trans-esterification reaction. In the first step, dimethyl terephthalate is ester interchanged with an excess of ethylene glycol at elevated temperatures. After the methyl ester groups have been replaced by hydroxy-ethyl ester groups, the excess ethylene glycol is removed by distillation. In the second step, the temperature is raised to about 280° C. and ethylene glycol is removed under vacuum until a polymer of the desired molecular weight is obtained.

Obviously, it would be more desirable to prepare the intermediate glycol terephthalates directly from terephthalic acid. However, the esterification of terephthalic acid with glycols is complicated by its poor solubility in the reaction mixture and satisfactory contact between the reactants is not obtained using conventional procedures. In one approach, the esterifying glycol is used in a large excess so that the product ester remains dissolved in the warm reaction mixture. Such reactions proceed extremely slow with the formation of large amounts of dialkylene glycols and similar ethers which ultimately become a part of the polyester polymer chain. The introduction of aliphatic ether linkages into the polymer causes the products made therefrom to exhibit poor stability to light and washing, inferior wash-and-wear properties, and accelerated dye fading. In short, the presence of excess ether groups makes the product polyester unsuitable for fiber and film production.

The rate of esterification of the terephthalic acid by conventional procedures is very slow, and in order to obtain substantially complete esterification, it has been necessary to continue refluxing the acid and the reactant glycol for some 72 hours. It is well known that such esterification processes may be expedited by the introduction of dehydrating compounds, the most commonly used being mineral acids such as sulfuric acid. However, such catalysts also promote the undesirable glycol etherification reaction and will cause discoloration or even charring in the subsequent polymerization step.

It has been recently discovered that terephthalic acid can be more rapidly esterified with a glycol by operating at temperatures above the normal boiling point of the glycol reactant, i.e., at superatmospheric pressures. It also has been discovered that the presence of an alkaline inorganic substance during esterification inhibits ether by-product formation. Usually a polycondensation catalyst, such as antimony trioxide, is added, and the intermediate glycol terephthalate formed by direct esterification is polycondensed to the final polyalkylene terephthalate product.

Integration of the esterification and the polymerization steps has, apart from making the presence of an acidic esterification catalyst particularly undesirable, the effect of making the purity of the terephthalic acid employed a most important consideration. Any undesirable impurities initially present in the reactant acid would be carried through into the final polymer where these impurities would cause discoloration and other undesirable side effects. For this reason, it is necessary to use terephthalic acid of high purity when making polymers suitable for use in film and textile applications by such an integrated process. The manufacture of terephthalic acid of a sufficiently high degree of purity has heretofore proved difficult and this is at least partly the reason that an indirect esterification method utilizing purified dialkyl ester has been employed commercially. However, improved methods for making terephthalic acid are now being developed to make the acid in the necessary degree of purity for use in integrated esterification and polymerization processes.

We have discovered an improved multi-stage process for direct esterification of terephthalic acid with a glycol and which utilizes a volatile organic base buffering agent to inhibit ether formation. Surprisingly, it has been further found that such a base, even when used in small amount, catalyzes the desired esterification reaction by substantially accelerating the rate of the desired esterification reaction. Our esterification process can be integrated with conventional polycondensation processes to produce a high purity polyalkylene terephthalate.

It is, therefore, an object of the present invention to provide an improved process for the direct esterification of terephthalic acid with an alkylene glycol.

It is another object of the invention to provide a direct esterification method that does not require the presence of a large excess of glycol in the esterification mixture.

It is a further object of the present invention to provide a comparatively rapid method for the esterification of terephthalic acid with glycols.

It is still another object of the invention to provide a method for the esterification of terephthalic acid with glycols to prepare intermediate hydroxyalkylene terephthalates in high yields and with minimum formation of ether by-products.

It is also an object of the present invention to provide an improved method for the preparation of film- and fiber-forming polyalkylene terephthalates.

The present invention is a method for the esterification of terephthalic acid with an alkylene glycol, particularly ethylene glycol, which comprises heating in a first stage 1 mole of terephthalic acid, with at least about 1.2 moles of the alkylene glycol and 0.01–1.0% based on the weight of the acid of a volatile organic base at a temperature between 240°–320° C. and at a pressure above the vapor pressure of the reactant alkylene glycol at the reaction gtemperature until about 75–85% of the acid groups initially present in the terephthalic acid have been esterified, and then maintaining the reaction mixture from the first stage in a second stage at a temperature between 240°–320° C. at a pressure less than the pressure of said first stage until at least about 95% of the acid groups initially present in the terephthalic acid have been esterified. More specifically, the pressure in said second stage is reduced to substantially atmospheric.

In a preferred embodiment, particularly when use is made of a relatively low mole ratio of the alkylene glycol to the terephthalic acid, the second stage is carried out by reducing the pressure, incrementally or continuously, until a substantially atmospheric pressure is attained while the temperature is maintained in the 240° to 320° C. range. In general, such an embodiment produces an ultimate polymer of higher molecular weight as evidenced by viscosity measurement. Such an embodiment includes, for example, a step wherein the product from the first stage is maintained at a pressure of at least about 25 psig but below the vapor pressure of glycol at from 240°–320° C. until up to about 90% esterification of the acid groups of the acid is effected, and the product of the first step is then maintained at a pressure of not substantially above atmospheric at from about 240° to 320° C. until at least 95% esterification of the acid groups of the terephthalic acid is effected.

Our invention is further illustrated by means of the following general discussion and examples.

On order to appreciate the present invention, it is necessary to understand that merely achieving the esterification of terephthalic acid with a glycol is not enough to provide a product which is suitable for the subsequent polycondensation reaction leading to the production of fiber- and film-forming materials. In order to achieve that ultimate objective, it is necessary that the acid be esterified to the desired degree as quickly as possible while at the same time eliminating to the greatest extent possible the occurrence of side reactions. A noteworthy effect of operation according to the method of the present invention is that the softening point of the resultant polymer is elevated. The softening point is a measure of the amount of impurities such as ethers present in the polyester and it is known that polymers having a lower softening point exhibit inferior properties with respect to light and weather stability.

Esterification and transesterification reactions are equilibrium reactions prompted by the presence of an excess of the reactant alcohol. In the production of polyalkylene terephthalates, bis-omega-hydroxyalkyl terephthalate or its low polymer is first produced, either by ester interchange of a dialkyl terephthalate or by the esterification of terephthalic acid both by means of excess glycol. Removal of the excess glycol and the additional glycol liberated during polycondensation in the second step yields a polyester wherein the mole ratio of glycol to acid approaches 1:1. Theoretically speaking, approximately molar equivalent amounts of the reactant glycol and acid are required; any glycol present in excess of the molar equivalent must be removed in the polymerization step. Accordingly, it is most desirable to conduct the initial esterification reaction using as little excess glycol as possible in order to minimize the amount of glycol to be removed in the subsequent polymerization step.

In the process of the present invention, the amount of glycol present should be in moderate excess with respect to the amount of terephthalic acid to be esterified. When less than about 1.2 moles of glycol per mole of acid is employed, there is a tendency to end up with unesterified acid groups because of the limited amount of glycol available for esterification. On the other hand, the presence of a substantial excess of glycol per mole of acid, in addition to being uneconomical, promotes the tendency toward the formation of undesired ether by-products. A ratio of about 1.3 to 1.7 moles of glycol per mole of acid, a range slightly above the minimum, is preferred.

The process of the present invention results in the formation of a prepolymer that is a mixed oligomeric ester. This prepolymer product can be transesterified to fiber-grade polyalkylene terephthalate under the customary reaction conditions with the minimum formation of undesirable by-products. For example, the conversion of alkylene glycols to dialkylene glycols is suppressed.

Although our invention is most often illustrated by use of ethylene glycol as the glycol reactant, any alkylene glycol, and preferably symmetrical difunctional glycols may be used. Particularly suitable are the lower alkylene glycols that contain 2 to 6, and preferably 2 to 4, carbon atoms or mixtures thereof. Such glycols include ethylene glycol, 1,3-propylene glycol, 1,4-butanediol, and mixtures thereof.

About 0.01–1.0% by weight of the organic base (molar ratio about 0.000116 to 0.0164:1 for triethylamine and tripropylamine) with respect to the terephthalic acid is added to the glycol-terephthalic acid reaction mixture prior to esterification. Superior results are obtained when the base is homogenized with the reactant glycol and acid. When less than 0.01% by weight of the base per weight of terephthalic acid initially present is employed, its effect and the pH of the reaction mixture are generally too low to minimize effectively the formation of ether by-products. On the other hand, while more than 1.0% of the base is also effective, there is a tendency for an undesirable amount of residual base to be present in the ultimate polymer and subsequent discoloration of the ultimate polymer. For example, in the use of triethylamine in an amount of 3% (i.e., -5 mol %) by weight of the terephthalic acid in a two-stage system as embodied herein, at the preferred operations at relatively high temperatures (e.g. 280° C.) the prepolymer product exhibits a yellowish discoloration. The preferred range is about 0.2–0.6% by weight of the base per unit weight of acid initially present.

The base employed is preferably a primary, secondary or tertiary alkyl amine and, as used herein, alkyl amines are intended to include cycloalkylamines. Since essentially all of the base is to be removed by volatilization, as for example, by distillation or evaporation, prior to polycondensation, the base should be more volatile than the reactant alkylene glycol or boil below the normal boiling point of that glycol. Examples of suitable amines include n-butyl amine, t-butyl amine, diisopropyl amine, di-n-propyl amine, di-n-butylamine, diisobutyl amine, triethylamine, tripropylamine and piperidine. Open-chain amines such as triethylamine, diisopropyl amine, di-n-butyl amine and tripropylamine which boil at a temperature intermediate between room temperature and the boiling point of the reactant alkylene glycol, are preferred as they give use to ultimate polymer products of superior color characteristics.

The reaction mixture, prepared as described above, is esterified in two stages and, as described hereinbefore, the second stage can comprise a multi-step operation. As compared to a single stage operation, operation in stages gives a faster overall reaction, extensive esterification of the acid groups present with less ether by-product formation and a superior overall product.

In the first stage, the reaction mixture is heated to a temperature between 240°–320° C., preferably 280° C. At temperatures below 240° C., the rate of esterification is too slow. The rate of reaction increases with temperature but at temperatures on the order of 320° C., and above, the rate of undesirable by-product formation (e.g., prepolymer degradation) tends to become significant even in the much shorter residence times required for 75–85% reaction of the acid groups initially present. The dependence of residence time on the temperature of reaction to achieve this degree of esterification is shown in the following table:

| Reaction Temperature | Residence Time |
| --- | --- |
| 240° C. | 1.5–3.0 hours |
| 260° C. | 0.5–1.0 hour |
| 280° C. | 5–15 minutes |
| 300° C. | 3–8 minutes |

The pressure employed in the first stage is controlled so as to keep most of the reactant glycol present in the reaction mixture while allowing a portion, and preferably a major portion, of the water in the reaction system to vaporize. This pressure has been determined to be above the vapor pressure of the alkylene glycol reactant at the reaction temperature and, in preferred embodiment, approximately 1–50 psig, and more preferably 5–10 psig, above that vapor pressure. At the preferred reaction temperature of about 280° C. to 290° C., the preferred pressure is about 120 to 150 psig. At reaction temperatures of 240° and 300° C., for example, the preferred pressures are 40 and 185 psig, respectively.

After about 75–85% of the acid groups initially present have been esterified in the first stage, the resultant reaction mixture is further esterified in the second stage until at least about 95% of the acid groups initially present have been esterified. The same 240°–320° C. reaction temperature range is employed but somewhat lower operating temperatures may be preferred. The reaction pressure is lower in the second stage to allow removal of water, buffer and unreacted glycol. Pressures in the range of below the vapor pressure of the reactant glycol at the reaction temperature down to substantially atmospheric pressure are now employed. A reaction pressure of about atmospheric is suitably utilized. The residence time of the reaction mixture in the second stage is not as critical as in the first stage. Generally the residence time in the second stage is about 0.5–3.0 times that in the first stage.

As described hereinbefore, the second stage can be carried out in at least two successive operations. For such an embodiment, the first step of the second stage is carried out at a preferred pressure of about 40 to 75 psig at 280° C. Under such conditions, sufficient alkylene glycol is retained in the reaction mixture to provide an ultimate prepolymer with a high ratio of glycol ended-:acid ended oligomers. Such oligomers having a ratio in excess of two have been found to be more readily polymerizable to higher molecular weight polyalkylene terephthalates, than in the case of oligomers having a lower ratio. Such higher molecular weight polymers are especially desirable in applications requiring high strength fibers, as for tire cord manufacture. The second step of the second stage is carried out by maintaining the product from the first step at substantially atmospheric pressure, e.g., 5 psig to -5 psig at 280° C.

On the other hand, the second stage can be carried out by continuous decrease of pressure, or by a combination of intermittent and continuous pressure decrease, until a substantially atmospheric pressure is attained. Optimum operation, insofar as use of intermittent, continuous, or combinations thereof for pressure reduction, will vary within the nature of equipment employed and viscosity requirements of the ultimate polymer product.

Use of the amine and the two stage esterification as described above results in a polyalkylene terephthalate prepolymer mixture suitable for polycondensation. Antimony trioxide or other suitable polycondensation catalyst is added to the reaction vessel at this point or may have been present in the initial esterification reaction mixture. Approximately 0.025 to 0.050% by weight of catalyst based on terephthalic acid charged is preferred. Using a temperature of about 280° C., the pressure is gradually reduced to below 10 mm Hg and preferably to below 1 mm. Nitrogen or other inert gas may be used to sparge the reaction mixture throughout all or a portion of this cycle. The pressure reduction and rate of sparging, when sparging is employed, are controlled to minimize the volatilization of polymer precursors, while glycol is removed. These conditions of temperature and pressure are maintained until a polymer of the requisite molecular weight, as determined by its viscosity or other convenient physical measurement, is obtained.

Preferably, the pressure in the polycondensation reaction vessel is then raised by means of an inert gas and the polymer melt discharged from the reactor through a series of small holes. The resulting strands are cooled and chopped into pellets suitable for remelting. Alternately, the polymer melt is conducted directly to an extruder or other polymer processing machinery and converted to finished articles such as film or fibers.

Our invention is further illustrated by the following examples:

In the experiments summarized below, ethylene glycol and terephthalic acid in a mole ratio of 1.5:1 were blended to a paste with or without an amine as indicated. The paste was placed in a 300° C. reactor with a pressure releasing device set at 150 psig and heated. When the reaction temperature of 280° C. was reached over a period of about 45 minutes, at which esterification to the extent of 75–85% was reached, the excess glycol and amine vapors present were vented while the reaction mixture was held at 280° C. for an additional 10 minutes. The prepolymer from each run was polycondensed with 0.025% by weight based on acid charged of antimony trioxide (polycondensation catalyst) for 3 hours at 285° C. under a vacuum of less than 0.1 mm of mercury.

| | | Prepolymer | | | Polymer Softening |
| --- | --- | --- | --- | --- | --- |
| Run | Amine Employed | % Ester | % Ether | RSY | Temp. ° C. |
| 1 | None | 97.5 | 5.5 | — | — |
| 2 | 0.28% diisopropyl amine | 97.8 | 2.0 | 1.28 | 266* |
| 3 | 0.50% diisopropyl amine | 95.4 | 2.0 | 1.06 | 266* |
| 4 | 0.25% di-n-butyl amine | 96.9 | 2.8 | 1.17 | 265* |
| 5 | 0.31% triethylamine | 96.5 | 3.1 | 1.24 | 265* |
| 6 | 0.28% diisobutyl amine | 95.7 | 2.2 | 1.24 | 255–257 |
| 7 | 0.28% n-butylamine | 96.5 | 2.2 | 0.89 | 256–258 |
| 8 | 0.28% tertiarybutyl amine | 96.5 | 2.2 | 1.13 | 254–256 |

*Crystalline melting point, ° C.
The per cent of the amine employed is by weight and with respect to the amount of terephthalic acid charge in the initial parts.

The following experiments illustrate the continuous preparation of hydroxyethylene terephthalate prepolymer according to the process of the present invention. Pastes containing mole ratios of ethylene glycol to terephthalic acid and percentages of amine and polycondensation catalyst as indicated were prepared in batches by means of a bakery mixer and stored in a 5 gallon hold tank. Paste from storage was continuously passed to the first reaction stage where it was quickly heated to the predetermined reaction temperature and held at a constant reaction pressure. The product from the first stage was passed to the second stage where the water of esterification, the amine and unreacted glycol were flashed off at about the same reaction temperature but at a lower reaction pressure.

In the runs summarized below, except as otherwise indicated, the amount of amine added was 0.28–0.56% by weight diisopropyl amine based on terephthalic acid charged. The molar ratio of ethylene glycol to acid ranged from 1.3–1.7:1.0. The pressure in the first stage was 150 psig and in the second stage 0 psig; the temperatures were approximately the same in both stages in any given run; and the residence time in the second stage was about twice that in the first stage for each run. Antimony trioxide, 0.025 or 0.050% by weight based on the terephthalic acid charged, was added prior to esterification and was the catalyst employed to polycondense the esterification product from each run.

| Run No. | Flow Rate gm/hr | EG/ TPA | Temp. ° C. | First Stage Product % Ester | First Stage Product % Ether | Second Stage Product % Ester | Second Stage Product % Ether |
|---|---|---|---|---|---|---|---|
| 1 | 2290 | 1.5 | 284 | 84.3 | 2.0 | 96.3 | 2.7 |
| 2 | 2550 | 1.3 | 287 | 84.0 | 1.5 | 96.3 | 2.3 |
| 3 | 3390 | 1.7 | 284 | 80.7 | 1.4 | 96.5 | 1.6 |
| 4 | 3650 | 1.5 | 289 | 82.6 | 2.0 | 96.1 | 2.6 |
| 5 | 3630 | 1.3 | 288 | 84.5 | 1.6 | 95.4 | 1.8 |
| 6 | 2600 | 1.5 | 289 | 83.6 | 1.6 | 96.4 | 2.2 |
| 7 | 2285 | 1.5 | 284 | 78.0 | 1.7 | 96.2 | 1.9 |
| 8 | 3630 | 1.5 | 300 | 83.1 | 2.0 | 96.2 | 2.7 |

In runs 3–6, 0.56% of amine was added, in runs 1, 2, 7 and 8, 0.28% of amine was employed. In run 7, no antimony trioxide was added. In run 8, the pressure in the first stage was 200 psig.

Using antimony trioxide as the polycondensation catalyst, prepolymers made as above were polycondensed to polymers low in ether content. Representative results are summarized in the table which appears below:

| Sample No. | % $Sb_2O_3$ | Prepolymer % Ether | Polymer % Ether |
|---|---|---|---|
| 1 | 0.05 | 1.8 | 2.2 |
| 2 | 0.025 | 2.3 | 2.3 |
| 3 | 0.025 | 1.7 | 1.7 |

In illustration of the embodiment wherein the second stage is carried out with pressure reduction in incremental manner, the following is set forth. In a 1-gallon autoclave, a mixture of terephthalic acid and ethylene glycol in a ratio of 1:1.5 and 0.28% diisopropylamine (based on the weight of the acid) was heated over a period of 15 minutes to 280° C. and maintained at 280° C., 150 psig for 15 minutes; then at 280° C. and 50 psig for 10 minutes; then at 280° C. at 0 psig for 10 minutes. The resultant prepolymer was polycondensed in a glass reactor for 3 hours at 280° C. under high vacuum (less than 0.1 mm Hg) to provide a polymer having a RSV of 1.32.

As stated hereinbefore, the use of amines as embodied herein, and as typified by use of diisopropyl amine in the following illustrations, results in the two-fold advantage of promoting the desired esterification reaction while suppressing the undesired ether formation.

In a continuous process for producing hydroxyethyl terephthalate prepolymer, terephthalic acid (1 mole) and ethylene glycol (1.5 mole) were separately fed to and mixed in a mixer and from which there was continually removed a slurry of acid and ethylene glycol in said mole ratio. The slurry was continuously fed to the first of a series of four reactors of which the first and second reactor comprised the first stage reaction as embodied herein. For said first stage reaction, the first of the first two reactors served to preheat the slurry to reaction temperature and to initiate the first stage esterification reaction. The pressure in the first reactor was controlled by the pressure in the second reactor. Operating conditions in the last three (termed for convenience as the second, third and fourth reactors) was as follows:

|  | Pressure (psig) | Temp. ° C. | Residence Time (mins) |
|---|---|---|---|
| Second Reactor | 100 | 270 | 15 |
| Third Reactor | 30 | " | " |
| Fourth Reactor | 2 | " | " |

During operation of the continuous process, diisopropyl amine (DIPA) in specified amount was introduced into the slurry prior to its entrance into the first reactor while, at times, the operation was carried out without addition of that amine. The following tabulation sets forth the results obtained with respect to the % esterification obtained, as to the product from the first reactor, with use of the stated amine (DIPA) versus omission of the amine under otherwise the same or substantially the same operating conditions.

| Run | Temp. in First Reactor (° C.) | DIPA based on acid (wt. %) | Pressure in First Reactor (psig) | Preheat Reaction Time in First Reactor (mins) | First Reactor Product % Esterification | First Reactor Product % Ether |
|---|---|---|---|---|---|---|
| (a) | 270 | 0 | 100 | 15 | 67.7 | 2.8 |
| (b) | " | 0.28 | " | " | 77.2 | 1.0 |
| (c) | " | 0 | 110 | 14 | 63.3 | 2.8 |
| (d) | " | 0.28 | " | 15 | 73.3 | 0.9 |

From the data in the foregoing tabulation, it can be seen that when the process was carried out without addition of the amine (Run a and c) the % esterification of the first reactor product was markedly lower than for the corresponding operation (Run b and d, respectively) carried out in presence of a small amount of the amine (0.28% based on weight of the acid). Expressed otherwise, at a pressure of 100 psig in the first reactor, 67.7% esterification was obtained (Run a) in absence of the amine whereas 77.3%, or about a 13% increase in esterification was obtained under the same conditions but in presence of the amine (Run b). Thus, for the same period of time, the amine functioned to markedly accelerate the esterification reaction. Taking into consideration that the uncatalyzed reaction (Run a) occurred at a substantially fast rate under the defined operating conditions, it should be apparent that the aforesaid increase in rate of esterification is a very significant and surprising result as to the catalytic effect of the amine with respect to the esterification reaction.

Similarly, comparison of the data set forth for Run (c) versus that for Run (d) shows the marked acceleration of the desired esterification reaction by use of the amine at somewhat higher operating pressure (110 psig) than for Runs (a) and (b). As is also set forth in the tabulation, the presence of the amine not only markedly increased the rate of desired esterification whereby a higher percentage of esterification was obtained in the same or similar period of time but, for both runs in which the amine was present, the esterification product was of markedly lower content of undesired ether than were the corresponding runs in absence of the amine. Additional runs using a higher concentration of the amine indicate that the catalytic effect of the amine on the rate of esterification generally increases as the amine concentration is increased.

In further illustration of the improvements obtained by practice of the present invention, the following tabulation sets forth results obtained with respect to undesired ether retardant and esterification catalysis effects by use of diisopropyl amine (DIPA), normal butyl amine (N-BA) and tripropyl amine (TrPA), as compared to the results obtained in absence of such amines, in esterifying terephthalic acid with ethylene glycol, at temperatures of 240° C. 260° C. and 280° C.

For the data set forth in the following tabulation, there was used a thin-walled stainless steel reactor 5⅜ inches in length and sealed at both ends with Swagelock caps (volume of 6.7 cc). Prior to sealing the reactor, there was charged five grams of a mixed blend of terephthalic acid:ethylene glycol of 1:1.5 mole ratio (in the runs without use of an amine), and in the case of runs with an amine, a total of five grams of acid:glycol in the aforesaid ratio plus the stated amount of amine based on the weight of the acid. The sealed tube was then immersed in a silicone oil bath at the stated temperature for the stated reaction time, followed by removal of the tube from the bath and immersion in an ice water bath to quench the reaction. Product was then removed from the tube and analyzed for % esterification and ether content. As is apparent from the data in the following tabulation, use of the amines exhibited the desirable dual effects of catalyzing the esterification reactions and suppressing ether formation.

TABULATION

| Temp. ° C. | Reaction Time (mins.) | Catalyst | Wt. % Catalyst | % Esterification | % Ether |
| --- | --- | --- | --- | --- | --- |
| 240 | 5.0 | None | — | 1.9 | <0.1 |
| 240 | 10.0 | None | — | 0 | <0.1 |
| 240 | 15.0 | None | — | 1.7 | <0.1 |
| 240 | 20.0 | None | — | 4.2 | 0.16 |
| 240 | 25.0 | None | — | 6.9 | 0.23 |
| 240 | 30.0 | None | — | 9.3 | 0.25 |
| 240 | 45.0 | None | — | 13.8 | 0.37 |
| 240 | 60.0 | None | — | 23.7 | 0.80 |
| 240 | 4.0 | DIPA | 0.5 | 0 | — |
| 240 | 8.0 | DIPA | 0.5 | 0.9 | — |
| 240 | 20.0 | DIPA | 0.5 | 2.3 | — |
| 240 | 30.0 | DIPA | 0.5 | 12.1 | — |
| 240 | 45.0 | DIPA | 0.5 | 22.4 | — |
| 240 | 60.0 | DIPA | 0.5 | 27.6 | — |
| 240 | 4.0 | N-BA | 0.5 | 0 | <0.1 |
| 240 | 8.0 | N-BA | 0.5 | 0 | <0.1 |
| 240 | 12.0 | N-BA | 0.5 | 4.0 | <0.1 |
| 240 | 16.0 | N-BA | 0.5 | 4.8 | <0.1 |
| 240 | 20.0 | N-BA | 0.5 | 9.3 | <0.1 |
| 240 | 30.0 | N-BA | 0.5 | 11.7 | 0.10 |
| 240 | 45.0 | N-BA | 0.5 | 19.6 | 0.20 |
| 240 | 60.0 | N-BA | 0.5 | 24.8 | 0.37 |
| 240 | 4.0 | TrPA | 0.5 | 0 | <0.1 |
| 240 | 8.0 | TrPA | 0.5 | 1.6 | <0.1 |
| 240 | 12.0 | TrPA | 0.5 | 7.4 | <0.1 |
| 240 | 16.0 | TrPA | 0.5 | 7.1 | <0.1 |
| 240 | 20.0 | TrPA | 0.5 | 8.1 | <0.1 |
| 240 | 30.0 | TrPA | 0.5 | 13.3 | <0.1 |
| 240 | 45.0 | TrPA | 0.5 | 22.3 | 0.17 |
| 240 | 60.0 | TrPA | 0.5 | 23.7 | 0.36 |
| 260 | 4.0 | None | — | 3.8 | <0.1 |
| 260 | 6.0 | None | — | 8.2 | 0.24 |
| 260 | 8.0 | None | — | 10.6 | 0.30 |
| 260 | 10.0 | None | — | 11.6 | 0.25 |
| 260 | 12.0 | None | — | 13.6 | 0.32 |
| 260 | 14.0 | None | — | 16.0 | 0.49 |
| 260 | 16.0 | None | — | 18.5 | 0.46 |
| 260 | 20.0 | None | — | 27.5 | 0.80 |
| 260 | 4.0 | DIPA | 0.5 | 3.7 | <0.1 |
| 260 | 6.0 | DIPA | 0.5 | 11.7 | 0.10 |
| 260 | 8.0 | DIPA | 0.5 | 15.0 | 0.23 |
| 260 | 10.0 | DIPA | 0.5 | 13.7 | 0.28 |
| 260 | 12.0 | DIPA | 0.5 | 19.5 | 0.38 |
| 260 | 14.0 | DIPA | 0.5 | 26.8 | 0.10 |
| 260 | 16.0 | DIPA | 0.5 | 25.1 | 0.26 |
| 260 | 20.0 | DIPA | 0.5 | 31.1 | 0.42 |
| 260 | 30.0 | DIPA | 0.5 | 47.2 | 0.80 |
| 260 | 4.0 | N-BA | 0.5 | 4.0 | <0.1 |
| 260 | 6.0 | N-BA | 0.5 | 5.6 | <0.1 |
| 260 | 8.0 | N-BA | 0.5 | 10.2 | <0.1 |
| 260 | 10.0 | N-BA | 0.5 | 17.8 | <0.1 |
| 260 | 12.0 | N-BA | 0.5 | 14.0 | 0.10 |
| 260 | 15.0 | N-BA | 0.5 | 26.5 | 0.17 |
| 260 | 20.0 | N-BA | 0.5 | 34.1 | 0.32 |
| 260 | 30.0 | N-BA | 0.5 | 44.9 | 0.67 |
| 260 | 4.0 | TrPA | 0.5 | 4.2 | <0.1 |
| 260 | 6.0 | TrPA | 0.5 | 7.8 | <0.1 |
| 260 | 8.0 | TrPA | 0.5 | 13.7 | <0.1 |
| 260 | 10.0 | TrPA | 0.5 | 15.8 | <0.1 |
| 260 | 12.0 | TrPA | 0.5 | 20.5 | 0.2 |
| 260 | 15.0 | TrPA | 0.5 | 30.1 | 0.2 |
| 260 | 20.0 | TrPA | 0.5 | 35.2 | 0.4 |
| 260 | 30.0 | TrPA | 0.5 | 40.0 | 0.7 |
| 280 | 4.0 | None | — | 8.4 | 0.6 |
| 280 | 6.0 | None | — | 15.4 | 0.8 |
| 280 | 8.0 | None | — | 23.1 | 1.1 |
| 280 | 10.0 | None | — | 32.1 | 1.6 |
| 280 | 12.0 | None | — | 24.8 | 1.5 |
| 280 | 14.0 | None | — | 37.1 | 1.9 |
| 280 | 20.0 | None | — | 40.8 | — |
| 280 | 4.0 | DIPA | 0.5 | 19.8 | 0.15 |
| 280 | 8.0 | DIPA | 0.5 | 23.8 | 0.40 |
| 280 | 12.0 | DIPA | 0.5 | 48.0 | 0.60 |
| 280 | 15.0 | DIPA | 0.5 | 51.0 | 1.00 |
| 280 | 16.0 | DIPA | 0.5 | 52.4 | 1.00 |
| 280 | 2.0 | N-BA | 0.5 | 0 | <0.1 |
| 280 | 4.0 | N-BA | 0.5 | 7.2 | <0.1 |
| 280 | 6.0 | N-BA | 0.5 | 19.4 | 0.12 |
| 280 | 8.0 | N-BA | 0.5 | 32.8 | 0.34 |
| 280 | 10.0 | N-BA | 0.5 | 44.3 | 0.50 |
| 280 | 12.0 | N-BA | 0.5 | 47.3 | 0.60 |
| 280 | 14.0 | N-BA | 0.5 | 48.8 | 0.80 |
| 280 | 16.0 | N-BA | 0.5 | 49.5 | 1.10 |
| 280 | 2.0 | TrPA | 0.5 | 0 | <0.1 |
| 280 | 4.0 | TrPA | 0.5 | 5.6 | <0.1 |
| 280 | 6.0 | TrPA | 0.5 | 21.3 | 0.11 |
| 280 | 8.0 | TrPA | 0.5 | 36.0 | 0.30 |
| 280 | 10.0 | TrPA | 0.5 | 38.8 | 0.40 |
| 280 | 12.0 | TrPA | 0.5 | 49.1 | 0.50 |
| 280 | 14.0 | TrPA | 0.5 | 40.9 | 0.70 |
| 280 | 16.0 | TrPA | 0.5 | 44.8 | 0.90 |

An important advantage resulting from the process of the present invention is the high degree of esterification obtained while producing a prepolymer low in ether content. The use of two stages for esterification and small amounts of the amine during esterification enables the esterification reaction to proceed at a high temperature, and consequently low residence time, without undue formation of ether by-products. The relatively small amount of the amine employed leaves only minimal residues in the ultimate polymer product and does not otherwise adversely affect the polycondensation reaction. The presence of the amine also inhibits corrosion in metal processing equipment.

The term RSV, used hereinbefore for viscosity values of the polymers, is represented by the following formula:

$$RSV = \frac{\frac{T_1}{T_0} - 1}{C}$$

wherein $T_1$ is the flow time for the polymer solution in seconds; $T_0$ is the flow time for the solvent in seconds; and C is the polymer concentration in grams/100 cc solvent. The viscosity determination is made by mixing, by weight, equal parts of phenol and tetrachloroethane at 50° C. to prepare the solvent solution, and adding 0.25 grams of polymers to 50 cc of the solvent solution. The resulting mixture is heated to 100° C. to dissolve the polymer. The resulting polymer solution is then cooled to room temperature and pipetted into a Cannon-Fenske viscometer Series No. 100. Viscosity is then measured at 25° C. (constant temperature bath) controlled to ± a tenth of a degree.

The above-offered discussion and examples have been presented for the purpose of illustrating the present invention. The invention is not dependent on any particular theoretical mode of operation or limited to the methods specifically illustrated above. Our invention is defined by the following claims:

We claim:

1. A method for the esterification of terephthalic acid with ethylene glycol which comprises
    heating, in a first stage, 1.0 mole of terephthalic acid, 1.3 – 1.7 mole of ethylene glycol and 0.01 to 0.6% based on the weight of said acid of an alkyl amine having a normal boiling point below about 200° C, at a temperature about 260° – 300° C and at a pressure above the vapor pressure of the glycol at the reaction temperature for 3 minutes to one hour until about 75 to about 85% of the acid groups initially present in the terephthalic acid have been esterified, and then
    maintaining the reaction mixture from the first stage in a second stage at a temperature about 260° – 300° C while reducing the pressure to substantially atmospheric until at least about 95% of the acid groups initially present in the terephthalic acid have been esterified.

2. A method according to claim 1 wherein about 0.2 to about 0.6% by weight of diisopropyl amine is present.

3. A method according to claim 2, wherein about 1.3 moles of ethylene glycol is present.

4. A method according to claim 1 wherein the residence time in the second stage is from about 0.5 to about 3 times the residence time in the first stage.

5. A method, as defined in claim 1, wherein the pressure reduction is carried out in stages.

6. A method, as defined in claim 1, wherein the pressure reduction is carried out substantially continuously.

7. A method according to claim 1 wherein the amine is a n-butylamine, tert-butylamine, diisopropyl amine, di-n-propyl amine, di-n-butyl amine, diisobutyl amine, tripropylamine or triethylamine.

8. A method according to claim 1 wherein said alkyl amine is present in an amount of 0.2 to 0.6% based on the weight of said acid.

9. In a method for preparing a filament-forming polyethylene terephthalate resin by forming an esterified terephthalate acid and polycondensing the resulting esterified terephthalic acid under reduced pressure at a polycondensation temperature in the presence of a polycondensation catalyst, the improvement which comprises forming the esterified terephthalate acid by
    heating in a first stage, one mole of terephthalic acid, 1.3 to 1.7 mole of ethylene glycol and 0.01 to 0.6% based on the weight of said acid of an alkyl amine having a normal boiling point below about 200° C at a temperature about 260° to 300° C and at a pressure above the vapor pressure of the glycol at the reaction temperature for three minutes to one hour until about 75 to 85% of the acid groups initially present in the terephthalate acid have been esterified, and
    maintaining the reaction mixture from the first stage in a second stage at a temperature of about 260° to 300° C while reducing the pressure to substantially atmospheric until at least about 95% of the acid groups initially present in the terephthalic acid have been esterified.

10. A method according to claim 9 wherein about 0.2 to about 0.6% by weight of diisopropylamine is present.

11. A method, according to claim 9, wherein about 1.3 moles of ethylene glycol is present.

12. A method, according to claim 9, wherein the residence time in the second stage is from about 0.5 to about 3 times the residence time in the first stage.

13. A method, as defined in claim 9, wherein the pressure reduction is carried out in stages.

14. A method, as defined in claim 9, wherein the pressure reduction is carried out substantially continuously.

15. A method according to claim 9 wherein said alkyl amine is present in an amount of 0.2 to 0.6% based on the weight of said acid.

16. A method according to claim 9 wherein said amine is n-butylamine.

17. A method according to claim 9 wherein said amine is tertiary-butylamine.

18. A method according to claim 9 wherein said amine is diisopropyl amine.

19. A method according to claim 9 wherein said amine is di-n-butylamine.

20. A method according to claim 9 wherein said amine is tripropylamine.

21. A method according to claim 9 wherein said amine is triethylamine.

* * * * *